(12) United States Patent
Fukuda et al.

(10) Patent No.: US 7,800,742 B2
(45) Date of Patent: Sep. 21, 2010

(54) CELL ANALYZER AND CELL ANALYZING METHOD

(75) Inventors: Masakazu Fukuda, Kobe (JP); Masaki Ishisaka, Himeji (JP)

(73) Assignee: Sysmex Corporation, Kobe (JP)

( * ) Notice: Subject to any disclaimer, the term of this patent is extended or adjusted under 35 U.S.C. 154(b) by 211 days.

(21) Appl. No.: 12/286,702

(22) Filed: Oct. 1, 2008

(65) Prior Publication Data
US 2009/0091746 A1    Apr. 9, 2009

(30) Foreign Application Priority Data
Oct. 3, 2007   (JP)   ............................. 2007-259777
Aug. 29, 2008  (JP)   ............................. 2008-222537

(51) Int. Cl.
*G01N 21/64* (2006.01)
*G01N 21/17* (2006.01)

(52) U.S. Cl. .................. 356/73; 356/317; 356/318; 356/336; 356/343; 436/164; 436/172

(58) Field of Classification Search .................. 356/72, 356/73
See application file for complete search history.

(56) References Cited

U.S. PATENT DOCUMENTS 5,050,987 A     9/1991  Kosaka
6,713,019 B2 *  3/2004  Ozasa et al. ............. 422/82.09

* cited by examiner

*Primary Examiner*—F. L Evans
(74) *Attorney, Agent, or Firm*—Brinks Hofer Gilson & Lione

(57) ABSTRACT

The present invention is to present a cell analyzer capable of measuring cells which are approximately 20 to 100 μm in size with high precision via flow cytometry. The cell analyzer 10 comprises: a flow cell 51 in which a measurement sample including a measurement target cell flows; a light source part 53 for irradiating a light on the measurement sample flowing in the flow cell 51; an optical system 52 for forming a beam spot on the measurement sample flowing in the flow cell 51, the beam spot having a diameter of 3~8 μm in a flow direction of the measurement sample and a diameter of 300~600 μm in a direction perpendicular to the flow direction of the measurement sample; and a light receiving part 55, 58, 59 for receiving a light from the measurement sample.

20 Claims, 14 Drawing Sheets

CELL ANALYZER AND CELL ANALYZING METHOD

RELATED APPLICATIONS

This application claims priority under 35 U.S.C. §119 to Japanese Patent Application Nos. JP2007-259777 filed Oct. 3, 2007, and JP2008-222537 filed on Aug. 29, 2008, the entire contents of which are hereby incorporated by reference.

FIELD OF THE INVENTION

The present invention relates to a cell analyzer and cell analyzing method. More specifically, the present invention relates to a cell analyzer and cell analyzing method for analyzing cells contained in a measurement sample using the light from the measurement sample when the measurement sample flowing through a flow cell is irradiated with light.

BACKGROUND

U.S. Pat. No. 5,050,987 discloses an analyzer for measuring white blood cells and their nuclei contained in blood using scattered light and fluorescent light from a measuring sample by irradiating laser light on the measuring sample which includes blood cells via flow cytometry.

The flow cytometric method disclosed in U.S. Pat. No. 5,050,987 is used to measure white blood cells which are approximately 10 µm in size. In the analyzer disclosed in U.S. Pat. No. 5,050,987, it is therefore difficult to measure cells which are approximately 20 to 100 µm in size with high precision as in the case of, for example, epithelial cells of the uterine cervix.

An object of the present invention is to provide a cell analyzer and cell analyzing method capable of measuring cells which are approximately 20 to 100 µm in size with high precision via flow cytometry.

SUMMARY

A first aspect of the present invention is a cell analyzer, comprising: a flow cell in which a measurement sample including a measurement target cell flows; a light source part for irradiating a light on the measurement sample flowing in the flow cell; an optical system for forming a beam spot on the measurement sample flowing in the flow cell, the beam spot having a diameter of 3~8 µm in a flow direction of the measurement sample and a diameter of 300~600 µm in a direction perpendicular to the flow direction of the measurement sample; and a light receiving part for receiving a light from the measurement sample.

A second aspect of the present invention is a cell analyzing method for irradiating a light on a measurement sample flowing in a flow cell and analyzing a measurement target cell included in the measurement sample using a light from the measurement sample, comprising a step of forming a beam spot on the measurement sample flowing in the flow cell, the beam spot having a diameter of 3~8 µm in a flow direction of the measurement sample and a diameter of 300~600 µm in a direction perpendicular to the flow direction of the measurement sample.

DETAILED DESCRIPTION OF THE EMBODIMENTS

The embodiments of the cell analyzer and cell analyzing method of the present invention are described hereinafter with reference to the accompanying drawings.

[General Structure of the Cell Analyzer]

Figure 1:
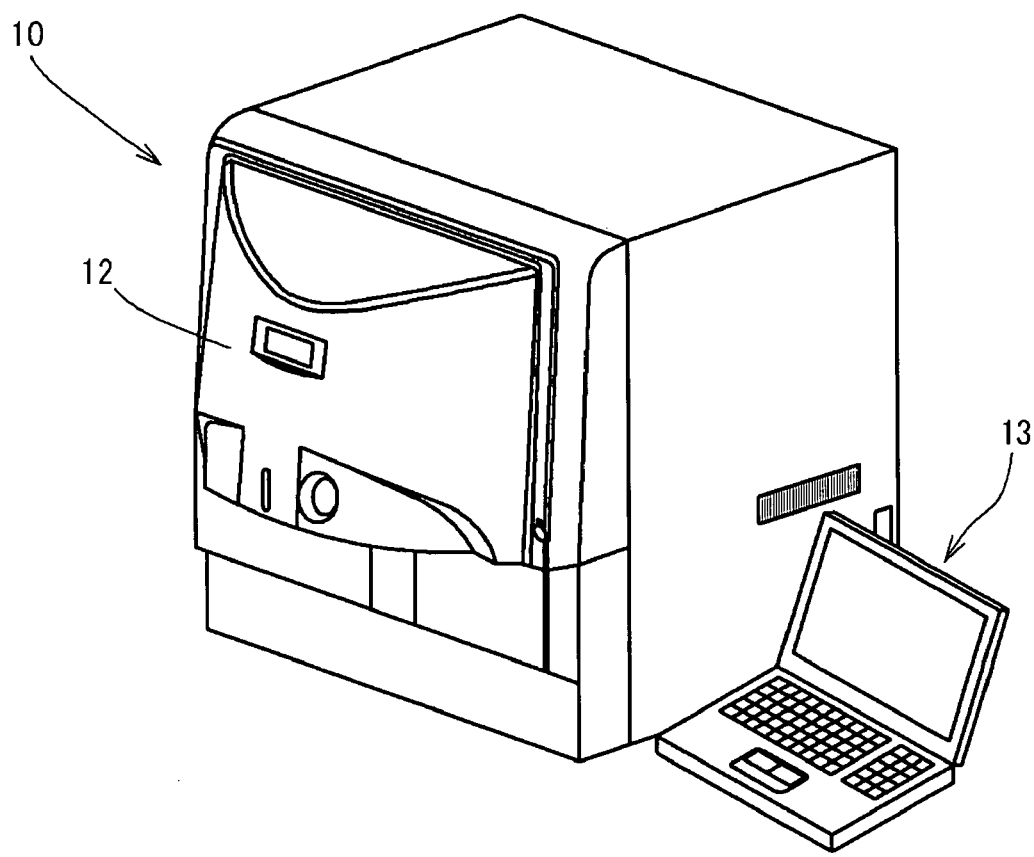
FIG. 1 is a perspective view of an embodiment of the cell analyzer of the present invention.

FIG. 1 is a perspective view of an embodiment of the cell analyzer 10 of the present invention. The cell analyzer 10 is used for determining whether or not cancerous or atypical cells are included among cells by flowing a measurement sample which includes cells collected from a patient in a flow cell, irradiating laser light on the measurement sample flowing in the flow cell, and detecting and analyzing the light (forward scattered light, side scattered light and the like) from the measurement sample. Specifically, the cell analyzer 10 is used for screening for cervical cancer using epithelial cells of the uterine cervix. The cell analyzer 10 is provided with an apparatus main body 12 for performing sample measurements and the like, and a system control part 13 for performing analysis of the measurement results and the like and which is connected to the apparatus main body 12.

Figure 2:
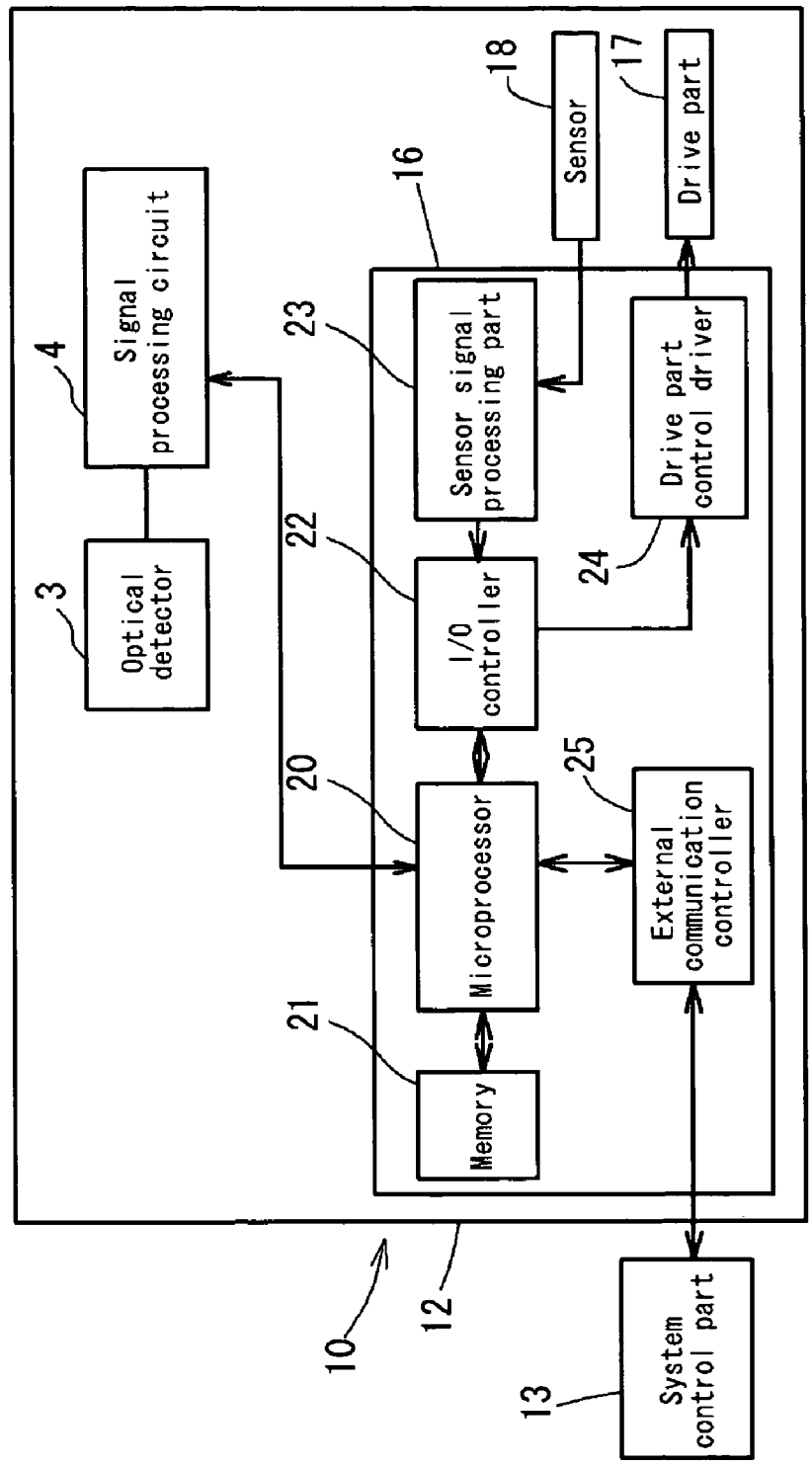
FIG. 2 is a block diagram showing the structure of the cell analyzer of FIG. 1.

FIG. 2 is a block diagram showing the structure of the cell analyzer of FIG. 1. The apparatus main body 12 of the cell analyzer 10 is provided with an optical detector 3 for detecting cells and information such as the size of the nuclei and the like from the measurement sample, a signal processing circuit 4, measurement control part 16, a drive part 17 such as a motor, actuator, valves and the like, and various sensors 18. The signal processing circuit 4 is provided with an analog signal processing circuit for amplifying and filter processing of the output of the optical detector 3 which have been amplified by a preamp (not shown in the drawing), an A/D converter for converting the output of the analog signal processing circuit to digital signals, and a digital signal processing circuit for performing predetermined waveform processing on the digital signals. The measurement control part 16 performs aspiration and measurement of the measurement sample by controlling the operation of the drive part 17 while processing the signals of the sensors 18. When screening for cervical cancer, a sample prepared by well known processing such as centrifuging (concentrating), diluting (washing), mixing, and propidium iodide (PI) staining and the like of cells (epithelial cells) collected from the uterine cervix of a patient may be used as the measurement sample. The prepared measurement sample is accommodated in a test tube and placed at a position below a pipette (not shown in the drawing) of the apparatus main body 12, and then is aspirated by the pipette and supplied to the flow cell. The PI staining is performed by propidium iodide, a fluorescent staining liquid. In PI staining, the fluorescent light from the nucleus becomes detectable since the nucleus is selectively stained.

[Structure of the Measurement Control Part]

The measurement control part 16 is provided with a microprocessor 10, memory 21, I/O controller 22, sensor signal processor 23, drive part control driver 24, external communication controller 25 and the like. The memory 21 is configured of RAM, ROM and the like, and the ROM stores a control program for controlling the drive part 17, and data required for the execution of the control program. The microprocessor 20 is capable of directly executing the control program from the ROM or loading the control program in the RAM.

Sensor signals are transmitted to the microprocessor 20 through the sensor signal processor 23 and the I/O controller 22. The microprocessor 20 can control the drive part 17 through the I/O controller 22 and the drive part control driver 24 according to the signals of the sensors 18 by executing the control program. The data processed by the microprocessor 20 and the data required for processing by the microprocessor 20 are transmitted and received to/from external devices such as the system control part 13 and the like through the external communication controller 25.

[Structure of the System Control Part]

Figure 3:
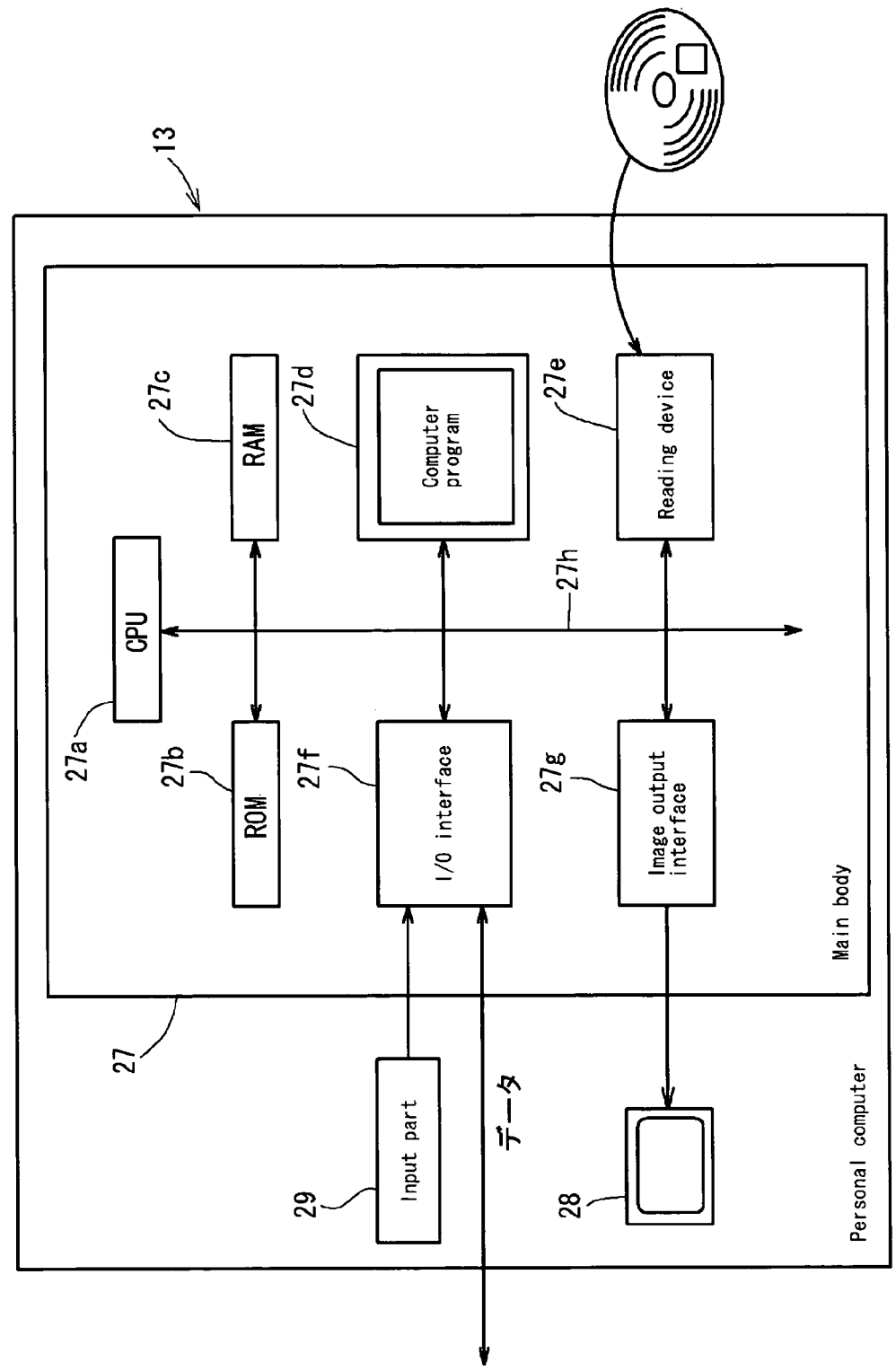
FIG. 3 is a block diagram of a personal computer which configures a system control part.

FIG. 3 is a block diagram of the system control part 13. The system control part 13 is configured by a microcomputer and the like, and is mainly configured by a body 27, display part 28, and input part 29. The body 27 is mainly configured by a CPU 27a, ROM 27b, RAM 27c, hard drive 27d, reading device 27e, input/output (I/O) interface 27f, and image output interface 27g. The parts are all connected via a bus 27h so as to be capable of communication.

The CPU 27a is capable of executing computer programs stored in the ROM 27b, and computer programs loaded in the RAM 27c. The ROM 27b is configured by a mask ROM, PROM, EPROM, EEPROM or the like, and stores computer programs executed by the CPU 27a and data and the like used in conjunction therewith. The RAM 27c is configured by SRAM, DRAM or the like. The RAM 27c is used when reading the computer programs recorded in the ROM 27b and stored on the hard drive 27d. The RAM 27c is also used as a work area of the CPU 27a when the computer programs are being executed.

The hard drive 27d contains various installed computer programs to be executed by the CPU 27a such as an operating system and application program and the like, as well as data used in the execution of these computer programs. An operating system which provides a graphical user interface environment, for example, Windows (registered trademark) or the like, a product of Microsoft Corporation, USA, is installed on the hard disk 27d. An operation program for transmitting measurement data (operation instructions) to the measurement control part 16 of the cell analyzer 10, receiving and processing the measurement results measured by the apparatus main body 12, and displaying the processed analysis results and the like is also installed on the hard disk 27d. The operation program operates on the operating system.

The reading device 27e is configured by a floppy disk drive, CD-ROM drive, DVD-ROM drive or the like, and is capable of reading the computer programs and data stored on a portable recording medium.

The I/O interface 27f is configured by a serial interface such as a USB, IEEE1394, RS232C or the like, parallel interface such as SCSI, IDE, IEEE1284 or the like, analog interface such as a D/A converter, A/D converter or the like. The I/O interface 27f is connected to the input part 29 which is configured by a keyboard and mouse, so that data can be input to the personal computer when a user uses the input part 29. The I/O interface 27f also is connected to the apparatus main body 12, and can transmit and receive data and the like to/from the apparatus main body 12.

The image output interface 27g is connected to the display part 28 which is configured by an LCD, CRT or the like, and outputs image signals according to the image data received from the CPU 27a to the display part 28. The display part 28 is configured so as to display an image (screen) based on the input image signals.

[Structure of the Optical Detector]

Figure 4:
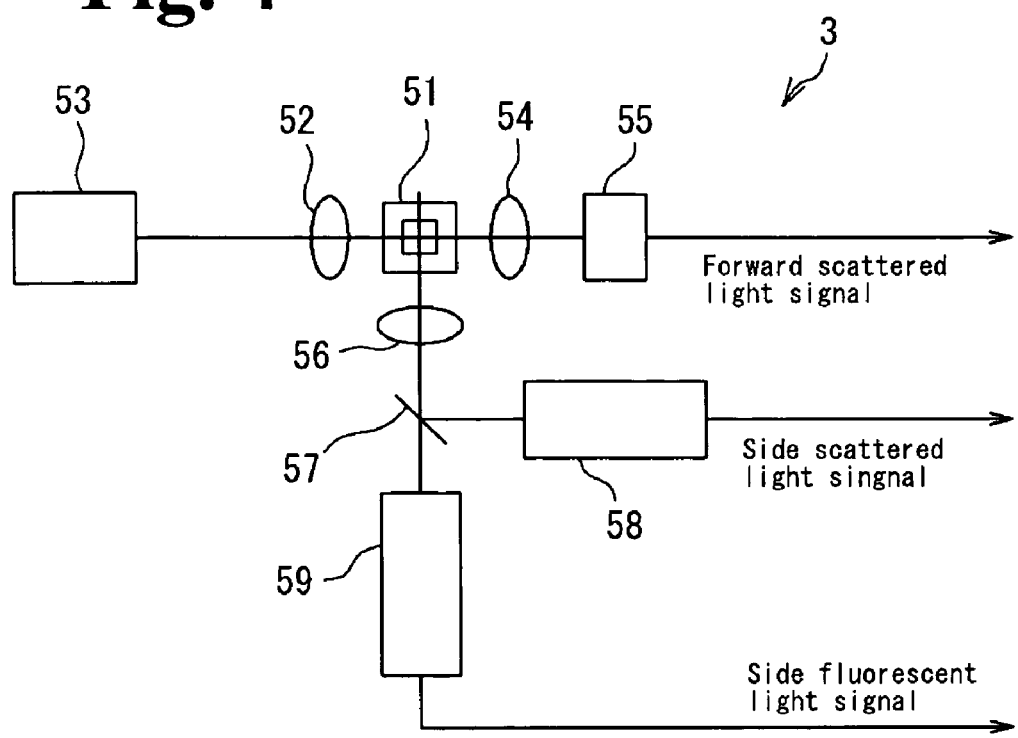
FIG. 4 shows the structure of an optical detector.

FIG. 4 shows the structure of an optical detector 3. In the drawing, a lens system (optical system) 52 collects the laser light emitted from a light source semiconductor laser 53, onto a measurement sample flowing in a flow cell 51, and a collective lens 54 collects the forward scattered light of the cell in the measurement sample on a photodiode 55, which is a scattered light detector. Although shown in the drawing as a single lens for simplicity, the lens system 52 more specifically can be configured as a lens group which includes, from the semiconductor laser 53 side, a collimator lens 52a, cylinder lens system (plano-convex cylinder lens 52b and biconcave cylinder lens 52c), and a condenser lens system (condenser lens 52d and condenser lens 52e), as shown in FIGS. 8 and 9.

Figure 8:
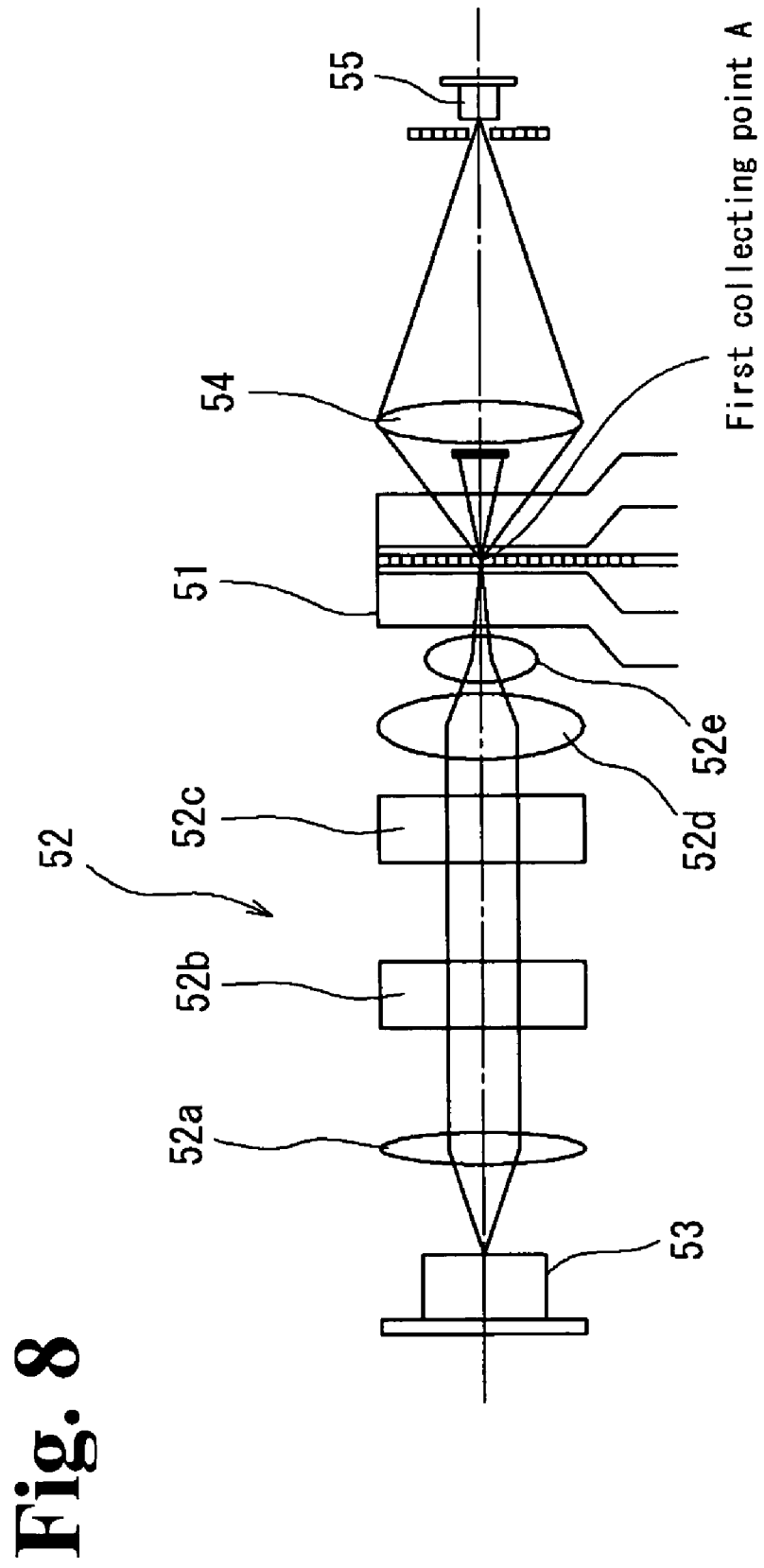
FIG. 8 is a side view of the structure of an optical detector.

When the optical detector 3 is viewed from the side surface as shown in FIG. 8, the radial laser light emitted from the semiconductor laser 53 is converted to parallel rays by the collimator lens 52a and passes through the plano-convex cylinder lens 52b and biconcave cylinder lens 52c without refraction, and is collected by the condenser lens 52d and the condenser lens 52e on the first collecting point A within the measurement sample flowing in the flow cell 51.

Figure 9:
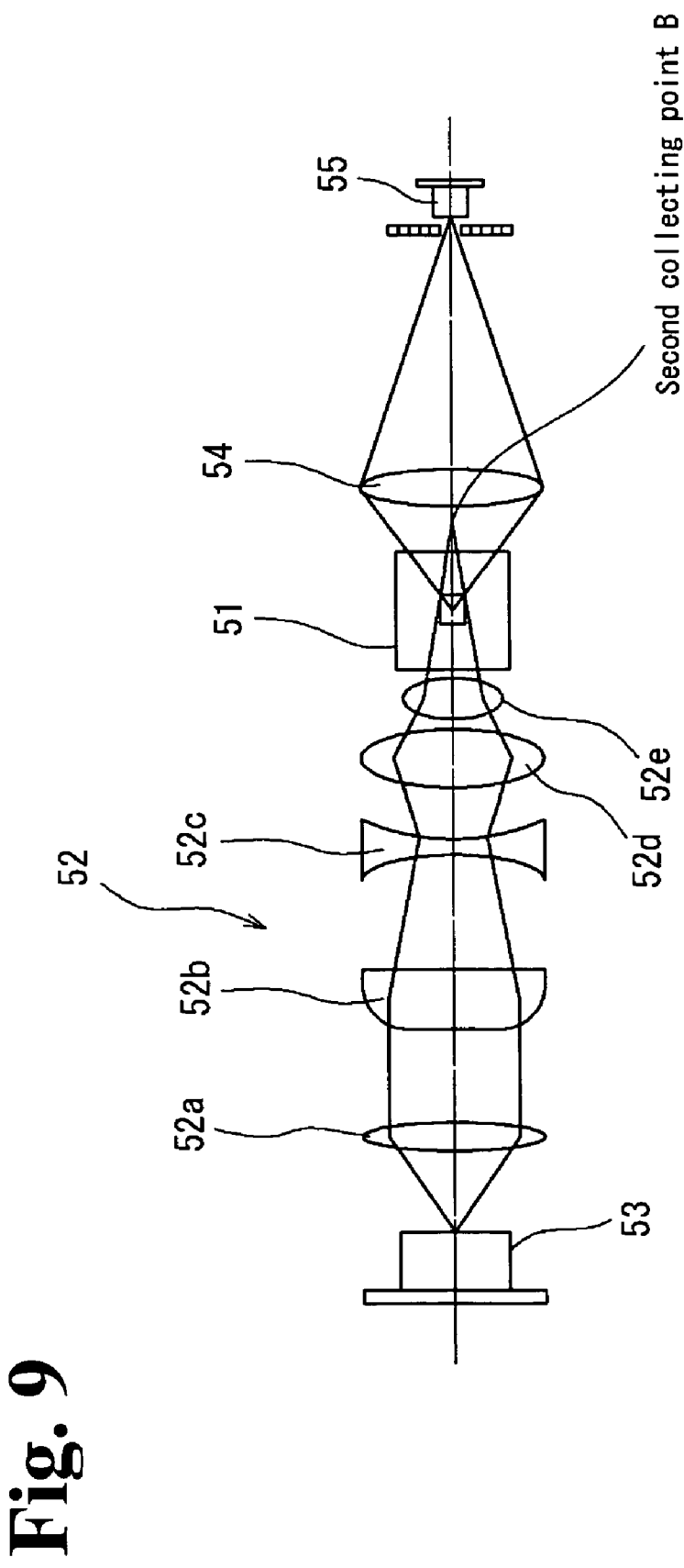
FIG. 9 is a top view of the structure of an optical detector.

On the other hand, when the optical detector 3 is viewed from the top as shown in FIG. 9, the radial laser light emitted from the semiconductor laser 53 is converted to parallel rays by the collimator lens 52a, converged in a direction perpendicular to the flow of the measurement sample by the plano-convex cylinder lens 52b and diverged in a direction perpendicular to the flow of the measurement sample by the biconcave cylinder lens 52c, and collected on a second collecting point B behind the flow cell 52 by the condenser lens 52d and condenser lens 52e.

The beam shape at the first collecting point A (beam shape when viewed from the semiconductor laser 53 side) is an elongated elliptical shape extending in a direction perpendicular to the flow of the measurement sample and converging in the direction of the flow of the measurement sample via the lens system 52. Specifically, a beam spot which has a diameter of 3 to 8 μm in the direction of the flow of the flow cell 51 and a diameter of 300 to 600 μm in a direction perpendicular to the flow of the measurement sample is irradiated on the measurement sample flowing in the flow cell 51 while forming the first collecting point A on the plane extending in the direction of the flow of the measurement sample.

Note that the lens system 52 is not limited to the structure described above and may be variously modified insofar as the light (beam spot) is formed on the measurement sample flowing in the flow cell so as to have a diameter of 3 to 8 μm in the direction of the flow of the measurement sample and a diameter of 300 to 600 μm in a direction perpendicular to the flow of the measurement sample.

The another collective lens 56 collects the side scattered light and side fluorescent light of the cell or the nucleus in the cell on a dichroic mirror 57. The dichroic mirror 57 reflects the side scattered light toward a photomultiplier 58 which is a scattered light detector, and allows passage of the side fluorescent light toward a photomultiplier 59 which is a fluorescent light detector. The light reflects the characteristics of the nucleus and the cell in the measurement sample. Then the photodiode 55, photomultiplier 58, and photomultiplier 59 convert the detected light to an electrical signals, and respectively output a forward scattered light signal (FSC) side scattered light signal (SSC), and side fluorescent light signal (SFL). These outputs are amplified by a preamp which is not shown in the drawing, and supplied to the previously mentioned signal processing circuit 4 (FIG. 2).

The forward scattered light data, side scattered light data, and side fluorescent light data (SFL) obtained by signal processing such as filter processing, A/D conversion processing and the like in the signal processing circuit 4 are transmitted to the previously mentioned system control part 13 through the external communication controller 25. In the system control part 13, a scattergram is created for analyzing the cell and nucleus based on the forward scattered light data, side scattered light data, and side fluorescent light data. The system control part 13 also determines whether or not the cell in the measurement sample is abnormal, specifically, whether or not the cell is a cancer cell or an atypical cell using the measurement data received from the signal processing circuit 4.

Note that although a gas laser may be used as the light source rather than a semiconductor laser, the use of a semiconductor laser is desirable from the perspective of low cost, compactness, and low power consumption, ands the use of a semiconductor laser can reduce the product cost and power consumption, and make the apparatus more compact. In the present embodiment, a blue light semiconductor laser is used which has a short wavelength that is advantageous in narrowing the beam. The blue light semiconductor laser is also effective relative to a fluorescent light excitation wavelength of PI and the like. Note that among semiconductor laser, a red light semiconductor lasers may also be used due to the stable supply from manufacturers, low cost, and long service life.

Figure 5:
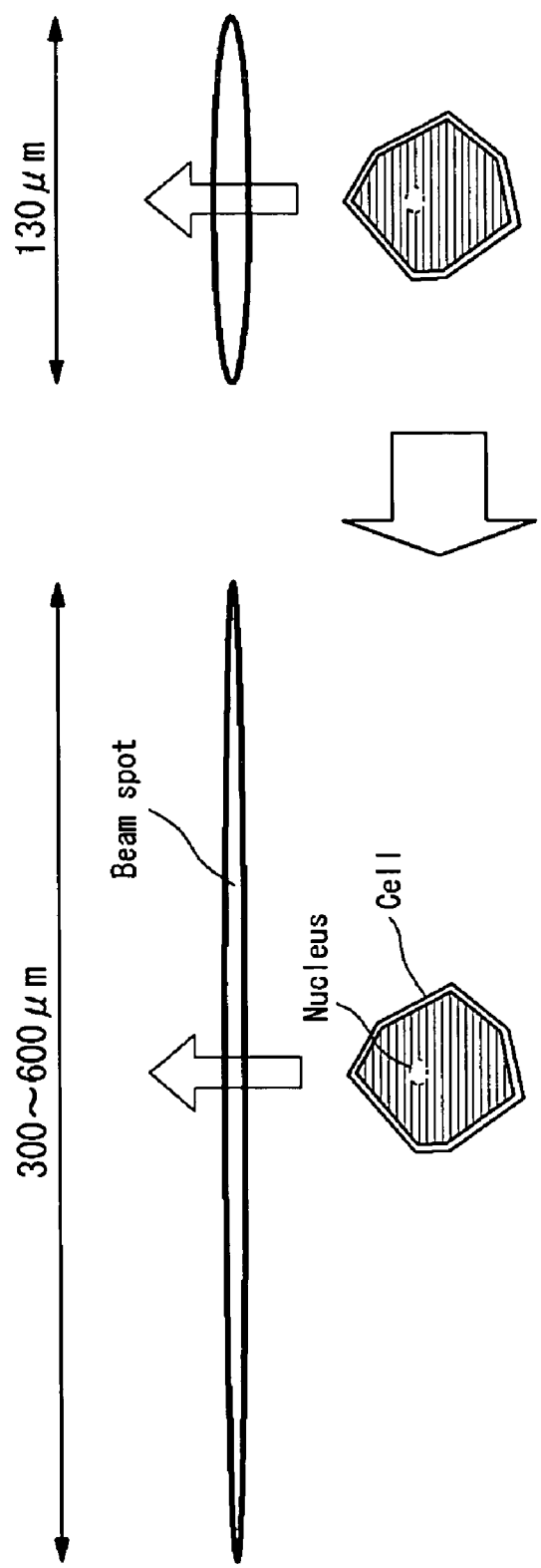
FIG. 5 illustrates a cell passing through a beam spot.

In the present invention a beam spot of a predetermined size is formed by the previously mentioned lens system 52 which is an optical system. Specifically, a substantially elliptical beam spot having a diameter of 3 to 8 μm in the direction of the flow of the measurement sample flowing in the flow cell and a diameter of 300 to 600 μm in a direction perpendicular to the flow of the measurement sample flowing in the flow cell is formed on the measurement sample. FIG. 5 illustrates a cell passing through the beam spot, and the vertical direction in the drawing is the direction of the flow of the measurement sample flowing in the flow cell. In FIG. 5, the beam spot on the right side is a beam spot in a typical conventional apparatus which is used to detect white blood cells and red blood cells in blood, and the beam spot on the left side is a beam spot formed by the optical system of the cell analyzer of the present invention. Although the dimension in the lengthwise direction of the beam spot is drawn more compact than the dimension in the direction (vertical direction in the drawing) perpendicular to the lengthwise direction according to the drawings, the actual beam spot of the present invention has an extremely long and narrow cross sectional shape.

The size of an epithelial cell in the uterine cervix is approximately 60 μm, and the size of the nucleus is 5 to 7 μm. When these cells become cancerous or atypical, cell division occurs with abnormal frequency and the size of the nucleus is 10 to 15 μm. The N/C ratio (size of the nucleus/size of the cell) is thus larger than that of a normal cell. The N/C ratio therefore can be used a determining index as to whether or not a cell is cancerous or atypical by detecting the size of the cell and the nucleus.

Figure 10:
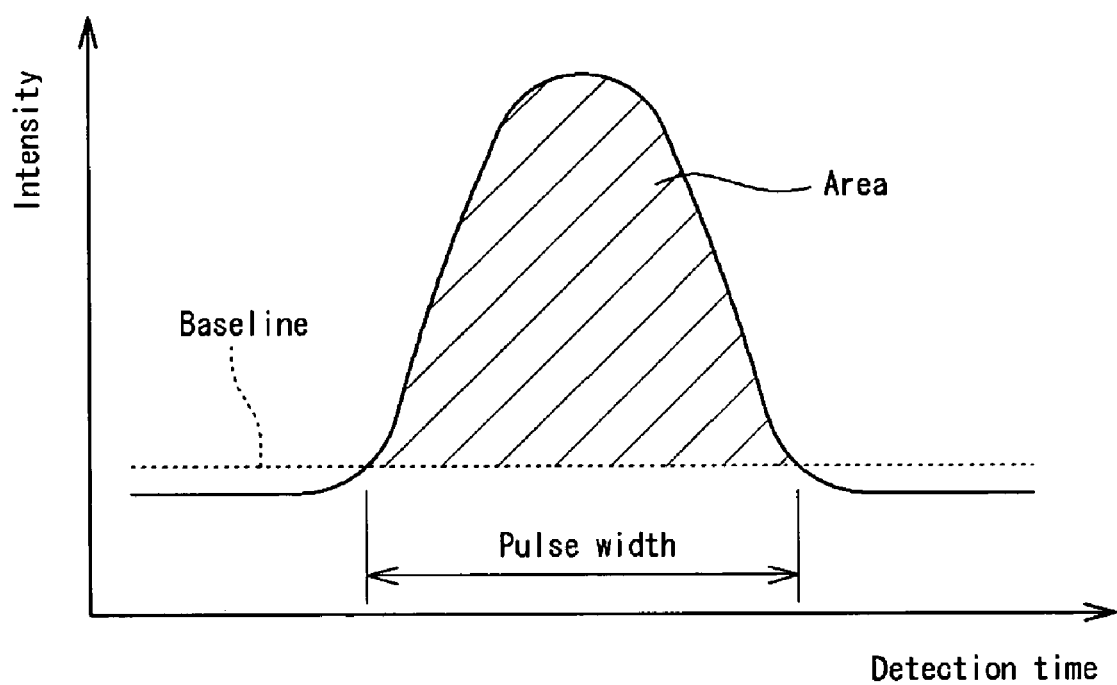
FIG. 10 illustrates the relationship between the signal waveform and the characteristic parameter.

In the present embodiment, the scattered light from the measurement sample flowing in the flow cell is detected by the photodiode 55, and the fluorescent light from the measurement sample flowing in the flow cell is detected by the photomultiplier 59; the signal processing circuit 4 obtains the pulse width of the scattered light signal which is a value reflecting the size of the measurement target cell from the scattered light signal output from the photodiode 55, and obtains the pulse width of a fluorescent light signal which is a value reflecting the size of the nucleus of the measurement target cell from the fluorescent light signal output from the photomultiplier 59. FIG. 10 shows a signal waveform of the light detected by the optical detector 3; the vertical axis shows the intensity of the detected light, and the horizontal axis shows the detection time of the light. As shown in FIG. 10, the pulse width represents the width of the signal waveform, and the width of the signal waveform which exhibits intensity greater than a baseline is used as the pulse width in the present embodiment. The baseline can be freely set. The pulse width of the scattered light signal indicates the transit time during which the measurement target cell passes through the sensing region in the flow cell, and the pulse width of the fluorescent light signal indicates the transit time during which the nucleus of the measurement target cell passes through the sensing region in the flow cell. The system control part 13 which is the analyzing part is configured to determine whether or not the measurement target cell is abnormal based on the value that reflects the size of the measurement target cell (pulse width of the scattered light signal) and the value that reflects the size of the nucleus of the measurement target cell (pulse width of the fluorescent light signal). Specifically, the system control part 13 determines that a measurement target cell is abnormal when a value obtained by dividing the pulse width of the fluorescent light signal divided by the pulse width of the scattered light signal is greater than a predetermined threshold value.

The S/N ratio of the nucleus detection can be improved and the size of the nucleus can be detected with high accuracy at the beam spot since the diameter is 3 to 8 μm in the direction of the flow of the measurement sample. Although the pulse width of the fluorescent light signal from the nucleus is used as a value reflecting the size of the nucleus in the present embodiment, fluorescent light from outside the nucleus is produced since the extra nuclear cell membrane outside the nucleus is slightly stained in PI staining, and residual stain used in staining flows through the flow cell. The photomultiplier 59 which is the fluorescent light detector therefore also detects the fluorescent light which is noise from outside the nucleus. However, the fluorescent light produced from the nucleus and the fluorescent light produced outside the nucleus can be sharply distinguished since the lens system 52 of the optical detector 3 reduces the diameter to 3 to 8 μm in the direction of flow of the measurement sample at the beam spot. That is, considering the size of a nucleus (5 to 7 μm), it is possible to sharpen the rise of the pulse of the fluorescent light signal and decrease the noise so that the pulse width can be measured more accurately by reducing the diameter of the beam spot to 3 to 8 μm. As a result, the size of the nucleus can be detected with high precision.

Figure 11:
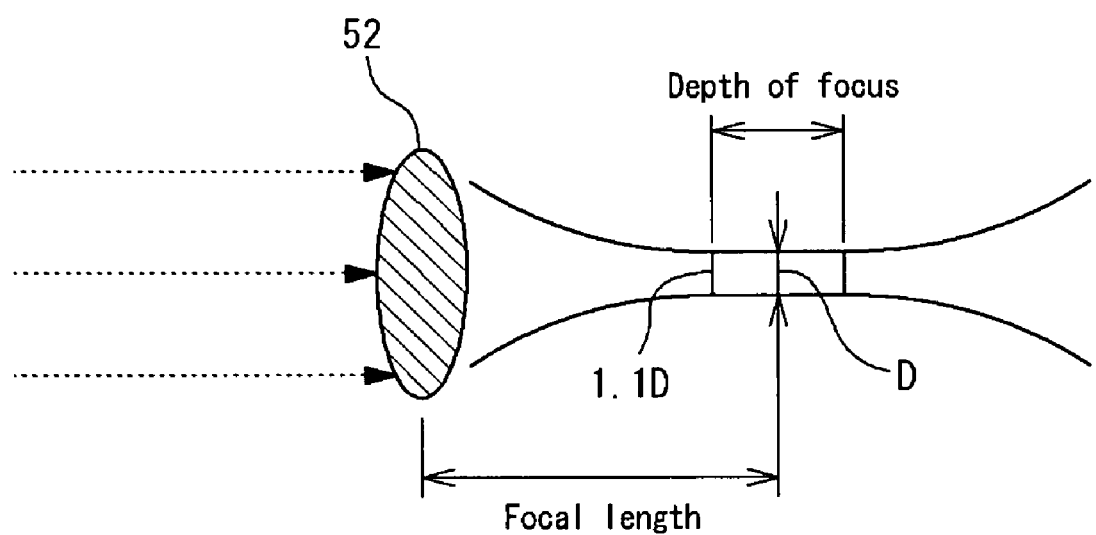
FIG. 11 shows a beam shape in the direction of the flow of the measurement sample.

When the diameter of the beam spot in the direction of the flow of the measurement sample is reduced to less than 3 μm, the focal length of the lens system 52 must be shortened, and the region of stable laser light intensity (depth of focus)

becomes shallower. FIG. 11 shows a beam shape in the direction of the flow of the measurement sample. As shown in FIG. 11, the depth of focus represents the range in which the beam diameter becomes 1.1 times the beam diameter D at the beam spot, and the light intensity decreases as the beam diameter increases. When the depth of focus becomes shallower, laser light cannot stably irradiate the nucleus of a cell which has a size of approximately 20 to 100 μm. On the other hand, when the diameter is greater than 8 μm in the direction of flow, there is an increase in the percentage of detected fluorescent light noise produced outside the nucleus. Therefore, measurement accuracy decreases because the rise of the pulse of the fluorescent light signal is smoothly gradual and the range of the pulse width of the fluorescent light signal becomes indistinct. There is also a high frequency of nuclei of a plurality of cells passing within the beam spot simultaneously, which also reduces measurement accuracy. Considering the depth of focus, it is therefore desirable to select the diameter of the beam spot in the direction of the flow of the measurement sample. Specifically, it is desirable to form the beam spot so that the depth of focus of the laser light converged in the direction of the flow of the measurement sample is 20 to 110 μm. Note that the diameter of the beam spot in the direction of the flow is desirably 3.5 to 7.5 μm, and more desirably 4 to 7 μm to stably irradiate the nucleus with laser light.

The entirety of the epithelial cell of the uterine cervix (approximately 60 μm) can pass through the stable region of the laser beam (the region of 0.95 or greater intensity when the peak intensity of the laser light forming a Gaussian distribution is designated 1) since the diameter of the beam spot is 300 to 600 μm in a direction perpendicular to the flow of the measurement sample. Stable scattered light from the cell is therefore obtained, and the size of the cell can be measured with high precision. When the diameter in a direction perpendicular to the flow is less than 300 μm, the stable region of the laser light becomes narrower, and stable scattered light from the cell cannot be obtained. On the other hand, when the diameter in a direction perpendicular to the flow is greater than 600 μm, the intensity of the laser light is reduced near the center, and stable scattered light cannot be obtained. Note that the diameter in a direction perpendicular to the flow of the measurement sample is desirably 350 to 550 μm in order to obtain stable scattered light from the cell.

[Cell Analyzing Method]

An embodiment of the cell analyzing method used in the cell analyzer 10 (FIG. 1) is described below.

First, the preparation of a measurement sample flowing in a flow cell is performed manually by a user. Specifically, a measurement sample is prepared by performing well know processes such as centrifuging (concentrating), diluting (washing), mixing, and PI staining cells (epithelial cells) collected from the uterine cervix of a patient. Then, the user accommodates the prepared measurement sample in a test tube (not shown in the drawing), and places the test tube at a position below the pipette (not shown in the drawing) of the apparatus body.

Figure 12:
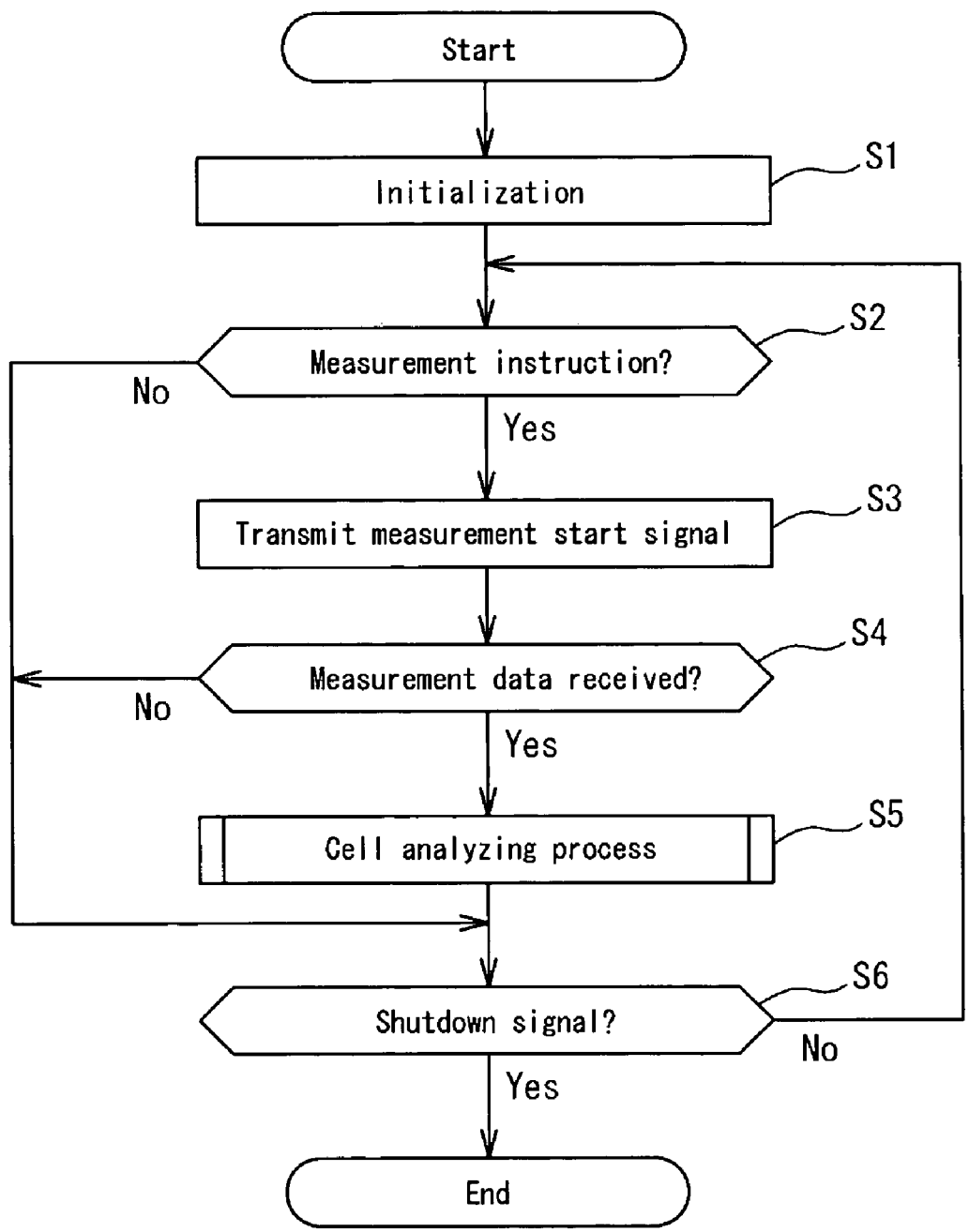
FIG. 12 is a flow chart showing the flow of the processing performed by the CPU of the system control part.
Figure 13:
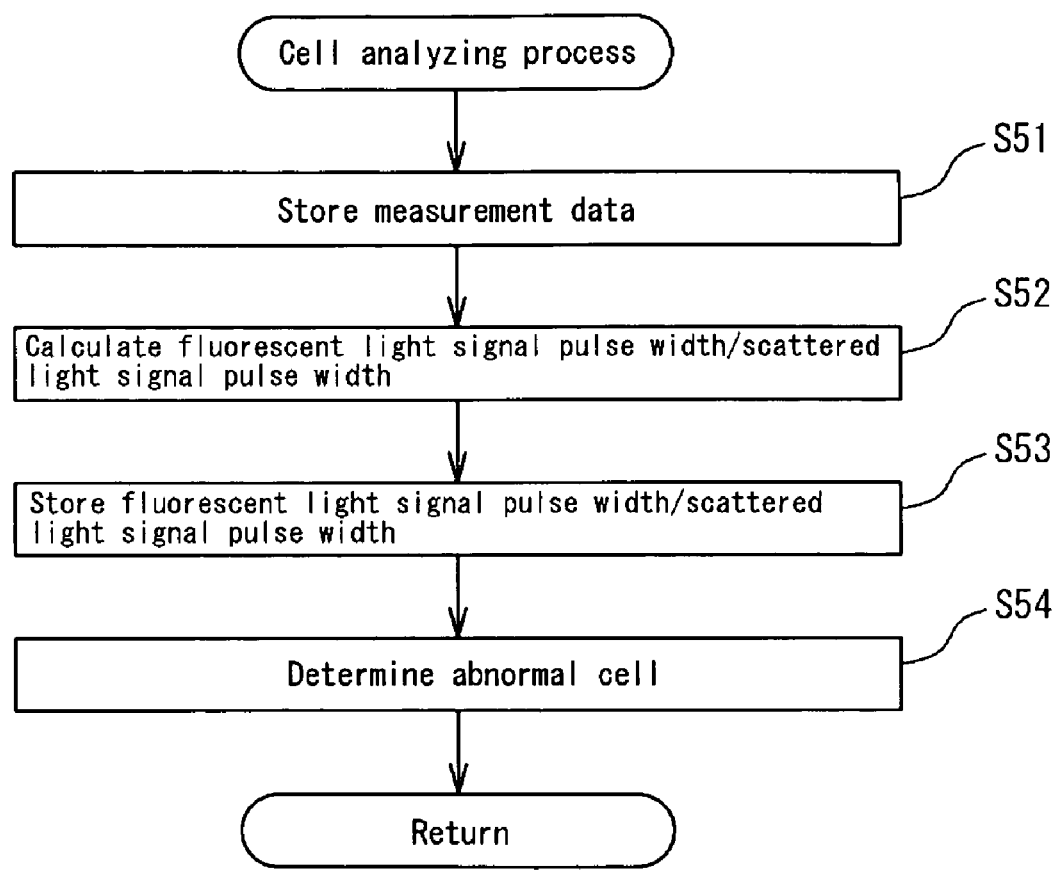
FIG. 13 is a flow chart showing the cell analysis process performed by the CPU of the system control part.

The flow of the processing performed by the system control part 13 is described below with reference to FIGS. 12 and 13. First, when the power supply of the system control part 13 is turned on, the CPU 27a of the system control part 13 initializes the computer program stored in the system control part 13 (step S1). Then, the CPU 27a determines whether or not a measurement instruction has been received from the user (step S2); when a measurement instruction has been received, a measurement start signal is transmitted to the apparatus main body 12 through the I/O interface 27f (step S3). When a measurement instruction has not been received, the CPU 27a moves to the process of step S6.

When a measurement start signal is transmitted to the apparatus main body 12, the measurement sample accommodated in the test tube is aspirated by the pipette and supplied to the flow cell 51 shown in FIG. 4 in the apparatus main body 12. Then, the measurement sample flowing in the flow cell 51 is irradiates by laser light, and the forward scattered light from the measurement sample is detected by the photodiode 55, the side scattered light is detected by the photomultiplier 58, and the side fluorescent light is detected by the photomultiplier 59.

Then, the forward scattered light signal (FSC), side scattered light signal (SSC), and side fluorescent light signal (SFL) output from the optical detector 3 are supplied to the signal processing part 4, and the measurement data obtained by performing predetermined processing in the signal processing part 4 are transmitted to the system control part 13 through the external communication controller 25.

In the other hand, the CPU 27a of the system control part 13 determines whether or not measurement data have been received from the apparatus main body 12 through the external communication controller 25 (step S4), and when measurement data have been received, the cell analyzing process is executed (step S5). When measurement data have not been received, the CPU 27a moves to the process of step S6.

After the cell analyzing process, the CPU 27a determines whether or not a shutdown instruction has been received (step S6), and the process ends when a shutdown instruction has been received. When a shutdown instruction has not been received, the CPU 27a returns to the process of step S2.

The cell analyzing process of step S5 is described below with reference to FIG. 13. First, the CPU 27a stores the measurement data received from the apparatus main body 12 on the hard disk 27d (step S51).

Then, the CPU 27a obtains a value (FSCW/SFLW) obtained by dividing the pulse width of the fluorescent light by the pulse width of the scattered light from the characteristic parameter information (pulse width (FSCW) of the scattered light signal) and the characteristic parameter information (pulse width (SFLW) of the fluorescent light signal) of the forward scattered light data included in the measurement data (step S52), and stores obtained value in the RAM 27c (step S53).

Then, the CPU 27a determines whether or not the cell is an abnormal cell (step S54) by comparing the value (FSCW/SFLW) obtained by dividing the pulse width of the fluorescent light by the pulse width of the scattered light to a predetermined threshold value T. In this case, the target cell is an abnormal cell when equation (1) is established, and the target cell is a normal cell when equation (1) is not established).

$$FSCW/SFLW \leq T \quad (1)$$

Although cancerous and atypical cells are determined from a value reflecting the size of the cell determined from scattered light and a value reflecting the size of the nucleus determined from fluorescent light in the above described embodiment, cancerous and atypical cells can also be determined by the size of the nucleus and the amount of nuclear DNA included in the nucleus. A second embodiment for determining cancerous and atypical cells from the size of the nucleus and the amount of nuclear DNA is described below.

In the apparatus main body 12 of the second embodiment, the photomultiplier 59 detects fluorescent light from a measurement sample flowing in a flow cell, and the signal processing part 4 obtains a value reflecting the amount of nuclear DNA and the size of the nucleus of a measurement target cell based on the fluorescent light signal output from the photomultiplier 59. As previously described, the pulse width (SFLW) of the fluorescent light signal can be set as the value reflecting the size of the nucleus of the cell, and the area (SFLI) of the pulse of the fluorescent light signal can be set as the value reflecting the amount of nuclear DNA. As shown in FIG. 10, the area (amount of fluorescent light) of the pulse of the fluorescent light signal represents the area of the part circumscribed by the baseline and the fluorescent light signal waveform. The baseline can be freely set. When a cell is cancerous or atypical, the result of cell division activity is an increase in the amount of DNA and increased size of the nucleus itself. Whether or not a cell is cancerous or atypical can therefore be determined with high precision by using both the size of the nucleus and the amount of DNA.

Figure 6:
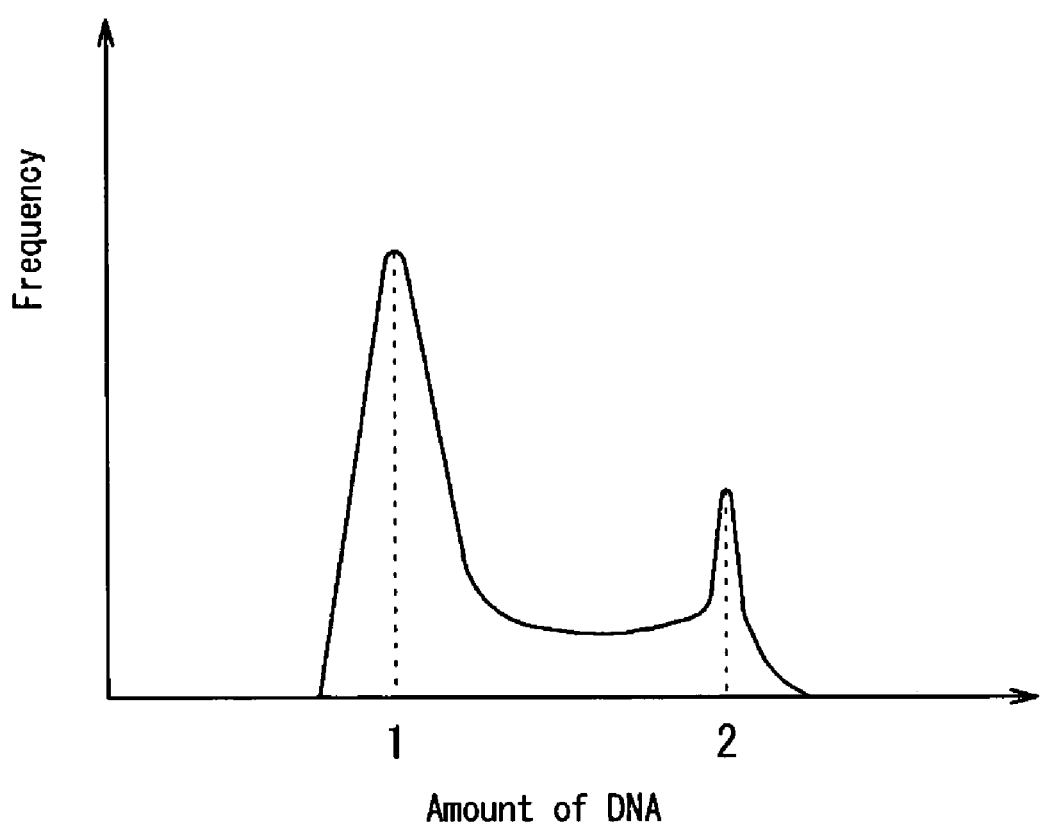
FIG. 6 shows an example of the distribution of the amount of DNA.

FIG. 6 shows an example of the distribution of the amount of DNA obtained by measuring a measurement sample of normal cells which are largely not cancerous or atypical; on the horizontal axis the amount of DNA peak occurrence frequency is set as [1], and double that amount of DNA is set as [2]. The peak on the left side indicates cells which are dividing normally. When a cell is cancerous or atypical, abnormal cell division occurs, and many distributions of cells have an amount of DNA which is on the right side of the position indicated by [2].

The CPU 27a of the system control part 13 executes a second cell analyzing process when measurement data including a pulse area (SFLI) of the fluorescent signal reflecting the amount of nuclear DNA and a pulse width (SFLW) of the fluorescent light signal reflecting the size of the nucleus obtained by the signal processing circuit 4 are received from the apparatus main body 12 through the external communication controller 25.

Figure 14:
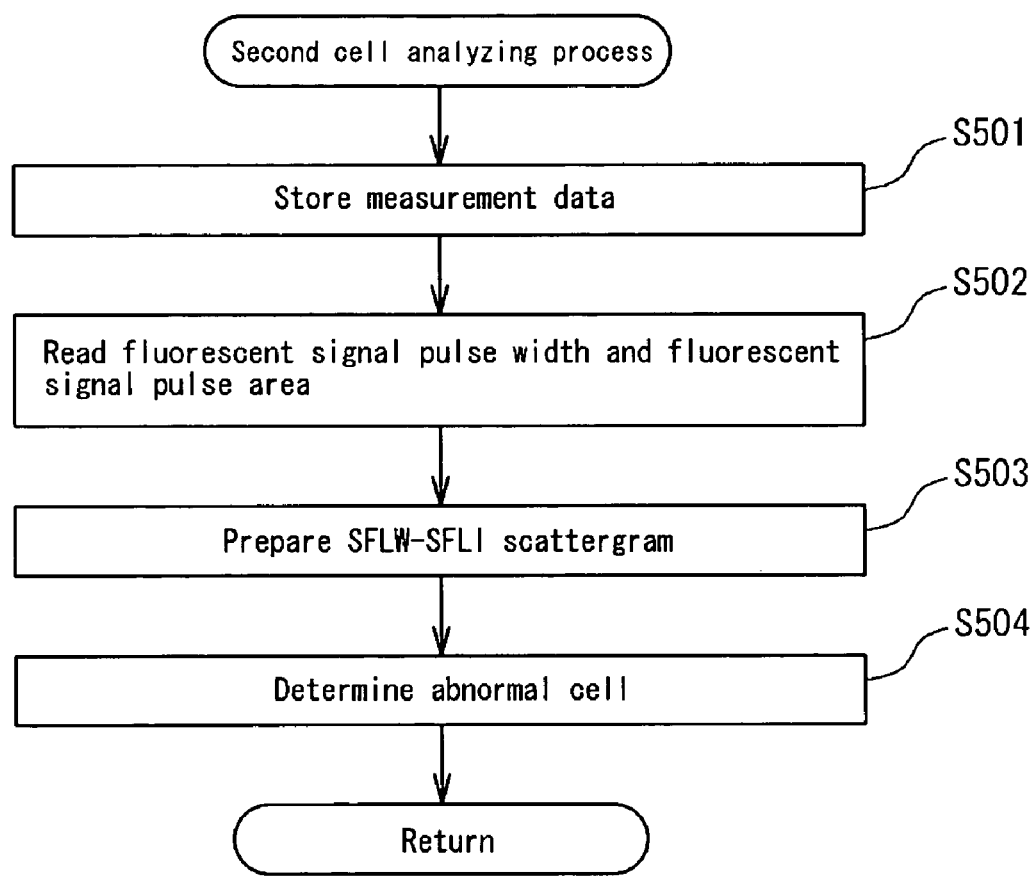
FIG. 14 is a flow chart showing a second cell analysis process performed by the CPU of the system control part.

FIG. 14 is a flow chart showing the second cell analyzing process performed by the CPU 27a of the system control part 13. The second cell analyzing process is described below with reference to FIG. 14. First, the CPU 27a stores the measurement data received from the apparatus main body 12 on the hard disk 27d (step S501).

Then, CPU 27a reads the characteristic parameter information (pulse width (SFLW) of the fluorescent signal and the pulse area (SFLI) of the fluorescent light signal) of the side fluorescent light data included in the measurement data to the RAM 27c (step S502).

Figure 7:
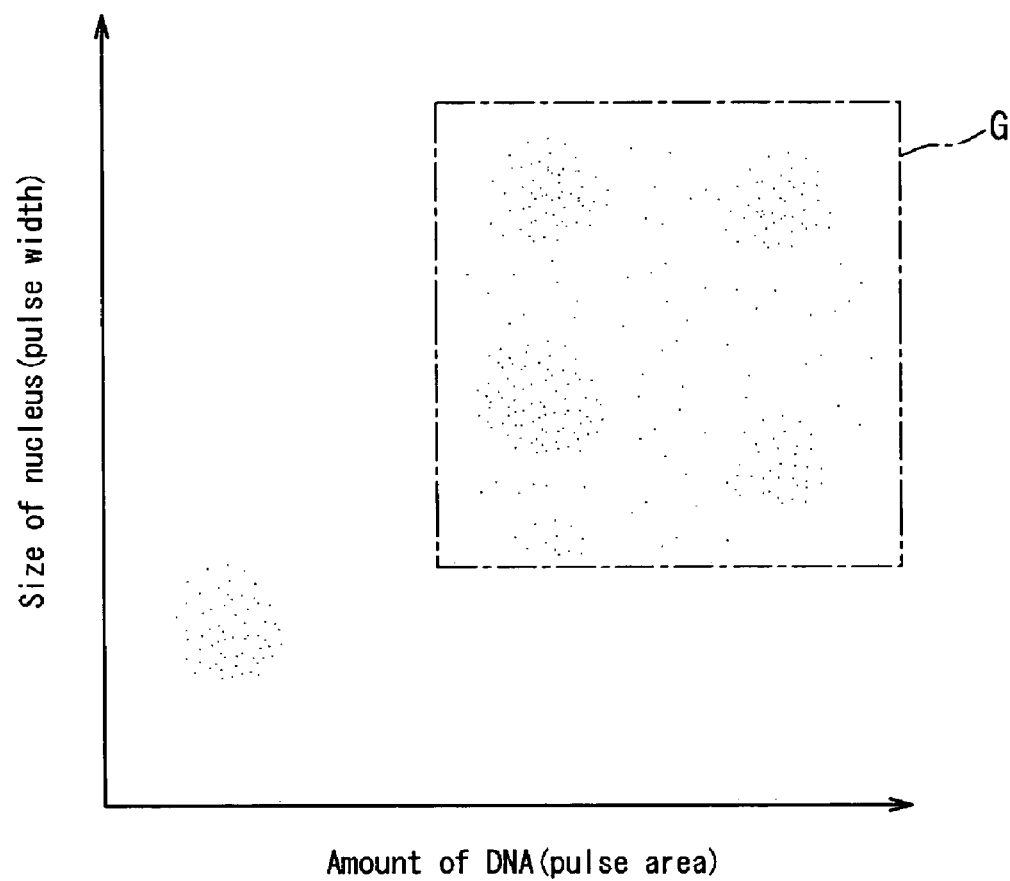
FIG. 7 is a scattergram showing the relationship between the amount of DNA and the size of the nucleus.

Then, the CPU 27a prepares a SFLW-SFLI scattergram plotting the pulse width (SFLW) of the fluorescent light signal on the vertical axis and plotting the pulse area (SFLI) of the fluorescent light signal on the horizontal axis (step S503). An example of the SFLW-SFLI scattergram is shown in FIG. 7. FIG. 7 shows the relationship between the size of the nucleus and the amount of DNA; the normal cell group is distributed in the region of the bottom left. When cells become cancerous or atypical, the nucleus becomes larger and the amount of DNA increases, and the cancerous and atypical cells are distributed in the region of the top right in FIG. 7. The size of the nucleus and amount of DNA therefore can be used to determine that the cells included in region G are cancerous and atypical.

Then, the CPU 27a determines whether or not the cell is an abnormal cell by comparing the pulse width (SFLW) of the fluorescent light signal to a predetermined threshold value M, and comparing the pulse area (SFLI) of the fluorescent light signal to a predetermined threshold value N (step S504). Specifically, the CPU 27a determines that the target cell is an abnormal cell when both equations (2) and (2) below are established, and determines that the target cell is normal when at least one of the equations (2) and (3) are not established.

$$SFLW \geq M \quad (2)$$

$$SFLI \geq N \quad (3)$$

Note that the embodiments disclosed herein are examples in all aspects and are not to be construed as limiting. The scope of the present invention is defined by the scope of the claims and not be the description of the embodiment, and includes all modifications within the scope of the claims and the meanings and equivalences therein.

For example, the present invention is not limited to detecting cancerous and atypical cells of the uterine cervix as in the above embodiments. Cancerous and atypical cells of the viscera, as well as buccal cells, and epithelial cells of the bladder, pharynx and the like may be detected.

Although the pulse width of the scattered light signal is used as the value reflecting the size of the measurement target cell, and the pulse width of the fluorescent light signal is used as the value reflecting the size of the nucleus of the measurement target cell in the present embodiment, the present invention is not limited to this arrangement. The pulse height of the scattered light signal may be used as the value reflecting the size of the measurement target cell, and the pulse height of the fluorescent light signal may be used as the value reflecting the size of the nucleus of the measurement target cell.

Although the measurement target cell is determined to be abnormal when a value obtained by dividing the value representing the size of the nucleus of the measurement target cell by the value representing the size of the measurement target cell is greater than a predetermined threshold value in the present embodiment, the present invention is not limited to this arrangement. The measurement target cell may also be determined to be abnormal when a value obtained by dividing a value representing the size of the measurement target cell by a value representing the size of the nucleus of the measurement target cell is less than a predetermined threshold value.

What is claimed is:

1. A cell analyzer, comprising:
   a flow cell in which a measurement sample including a measurement target cell flows;
   a light source part for irradiating a light on the measurement sample flowing in the flow cell;
   an optical system for forming a beam spot on the measurement sample flowing in the flow cell, the beam spot having a diameter of 3~8 μm in a flow direction of the measurement sample and a diameter of 300~600 μm in a direction perpendicular to the flow direction of the measurement sample; and
   a light receiving part for receiving a light from the measurement sample.

2. The cell analyzer of claim 1, wherein
   the light receiving part comprises a scattered light detector for detecting a scattered light from the measurement sample flowing in the flow cell, and a fluorescent light detector for detecting a fluorescent light from the measurement sample flowing in the flow cell;
   the cell analyzer further comprises:
   a signal processing part for obtaining a value reflecting a size of the measurement target cell from a scattered light signal output from the scattered light detector, and for obtaining a value reflecting a size of a nucleus of the measurement target cell from a fluorescent light signal output from the fluorescent light detector; and
   an analyzing part for determining whether or not the measurement target cell is abnormal, based on the value reflecting the size of the measurement target cell and the value reflecting the size of the nucleus of the measurement target cell obtained from the signal processing part.

3. The cell analyzer of claim 2, wherein
the signal processing part obtains a pulse width of the scattered light signal as the value reflecting the size of the measurement target cell, and obtains a pulse width of the fluorescent light signal as the value reflecting the size of the nucleus of the measurement target cell.

4. The cell analyzer of claim 3, wherein
the analyzing part is configured to determine that the measurement target cell is abnormal when a value obtained by dividing the pulse width of the fluorescent light signal by the pulse width of the scattered light signal is greater than a predetermined threshold value.

5. The cell analyzer of claim 3, wherein
the analyzing part is configured to determine that the measurement target cell is abnormal when a value obtained by dividing the pulse width of the scattered light signal by the pulse width of the fluorescent light signal is less than a predetermined threshold value.

6. The cell analyzer of claim 1, wherein
the optical system comprises a condenser lens system for collecting the light from the light source part onto the flow cell, and a cylindrical lens system for adjusting a diameter of the light from the light source part in a direction perpendicular to the flow of the measurement sample.

7. The cell analyzer of claim 6, wherein
the cylindrical lens system comprises a first cylindrical lens for converging the light from the light source part in the direction perpendicular to the flow of the measurement sample, and a second cylindrical lens for diverging the light from the light source part in the direction perpendicular to the flow of the measurement sample.

8. The cell analyzer of claim 1, wherein
the light receiving part comprises a fluorescent light detector for detecting a fluorescent light from the measurement sample flowing in the flow cell;
the cell analyzer further comprises:
a signal processing part for obtaining a value reflecting a size of a nucleus of the measurement target cell and a value reflecting amount of DNA in the nucleus of the measurement target cell from a fluorescent light signal output from the fluorescent light detector; and
an analyzing part for determining whether or not the measurement target cell is abnormal, based on the value reflecting the size of the nucleus of the measurement target cell and the value reflecting the amount of DNA in the nucleus of the measurement target cell obtained from the signal processing part.

9. The cell analyzer of claim 1, wherein
the beam spot is formed so that a depth of focus of the light converged in the flow direction of the measurement sample is 20 to 110 μm.

10. The cell analyzer of claim 1, wherein
the measurement target cell is an epithelial cell.

11. The cell analyzer of claim 10, wherein
the measurement target cell is an epithelial cell collected from an uterine cervix.

12. A cell analyzing method for irradiating a light on a measurement sample flowing in a flow cell and analyzing a measurement target cell included in the measurement sample using a light from the measurement sample, comprising a step of
forming a beam spot on the measurement sample flowing in the flow cell, the beam spot having a diameter of 3~8 μm in a flow direction of the measurement sample and a diameter of 300~600 μm in a direction perpendicular to the flow direction of the measurement sample.

13. The cell analyzing method of claim 12, further comprising steps of:
detecting a scattered light and a fluorescent light from the measurement sample flowing in the flow cell;
obtaining a value reflecting a size of the measurement target cell from a scattered light signal generated from the scattered light, and obtaining a value reflecting a size of a nucleus of the measurement target cell from a fluorescent light signal generated from the fluorescent light; and
determining whether or not the measurement target cell is abnormal, based on the value reflecting the size of the measurement target cell and the value reflecting the size of the nucleus of the measurement target cell.

14. The cell analyzing method of claim 13, wherein
the value obtaining step comprises a step of obtaining a pulse width of the scattered light signal as the value reflecting the size of the measurement target cell, and a step of obtaining a pulse width of the fluorescent light signal as the value reflecting the size of the nucleus of the measurement target cell.

15. The cell analyzing method of claim 14, wherein
the determining step comprises a step of determining that the measurement target cell is abnormal when a value obtained by dividing the pulse width of the fluorescent light signal by the pulse width of the scattered light signal is greater than a predetermined threshold value.

16. The cell analyzing method of claim 12, further comprising steps of:
detecting a fluorescent light from the measurement sample flowing in the flow cell;
obtaining a value reflecting a size of a nucleus of the measurement target cell and a value reflecting amount of DNA in the nucleus of the measurement target cell from a fluorescent light signal generated from the fluorescent light; and
determining that the measurement target cell is abnormal, based on the value reflecting the size of the nucleus of the measurement target cell and the value reflecting the amount of DNA in the nucleus of the measurement target cell.

17. The cell analyzing method of claim 12, wherein
the beam spot is formed so that a depth of focus of the light converged in the flow direction of the measurement sample is 20 to 110 μm.

18. The cell analyzing method of claim 12, wherein
the measurement target cell is an epithelial cell.

19. The cell analyzing method of claim 18, wherein
the measurement target cell is an epithelial cell collected from an uterine cervix.

20. The cell analyzing method of claim 13, further comprising a step of
selectively staining the nucleus of the measurement target cell using propidium iodide.

* * * * *